US005598848A

United States Patent [19]
Swanson et al.

[11] Patent Number: 5,598,848
[45] Date of Patent: Feb. 4, 1997

[54] SYSTEMS AND METHODS FOR POSITIONING MULTIPLE ELECTRODE STRUCTURES IN ELECTRICAL CONTACT WITH THE MYOCARDIUM

[75] Inventors: David K. Swanson, Mountain View; Dorin Panescu, Sunnyvale, both of Calif.

[73] Assignee: EP Technologies, Inc., Sunnyvale, Calif.

[21] Appl. No.: 221,347

[22] Filed: Mar. 31, 1994

[51] Int. Cl.[6] .................................................. A61B 5/04
[52] U.S. Cl. .......................... 128/696; 128/642; 128/734; 607/122
[58] Field of Search ..................................... 128/642, 696, 128/639, 734; 607/119, 122, 123, 124, 125, 126, 113, 116

[56] References Cited

U.S. PATENT DOCUMENTS

| 5,228,442 | 7/1993 | Imran | 607/122 |
|---|---|---|---|
| 5,293,869 | 3/1994 | Edwards et al. | 128/642 |
| 5,297,549 | 3/1994 | Beatty et al. | 607/122 |
| 5,309,910 | 5/1994 | Edwards et al. | 507/122 |
| 5,313,943 | 5/1994 | Houser et al. | 128/642 |
| 5,313,953 | 5/1994 | Yomtov et al. | 128/642 |
| 5,324,284 | 6/1994 | Imran | 607/122 |
| 5,341,807 | 8/1994 | Nardella | 128/642 |
| 5,345,936 | 9/1994 | Pomeranz et al. | 128/642 |
| 5,357,956 | 10/1994 | Nardella | 128/642 |

*Primary Examiner*—Lee S. Cohen
*Attorney, Agent, or Firm*—Ryan, Maki, Mann & Hohenfeldt

[57] ABSTRACT

Systems and methods evaluate electrical contact between the myocardium and one or more electrodes inside the heart. The systems and methods electrically sense electrical contact between the myocardium and electrodes and generate unitary contact-indicating outputs indicating the presence or absence of electrical contact between the myocardium and each particular electrode. The systems and methods also correlate the electrode-specific unitary outputs to generate a compound contact-indicating output. The compound output represents the aggregate of the electrical contact between the myocardium and multiple electrodes on a multiple electrode array.

32 Claims, 13 Drawing Sheets

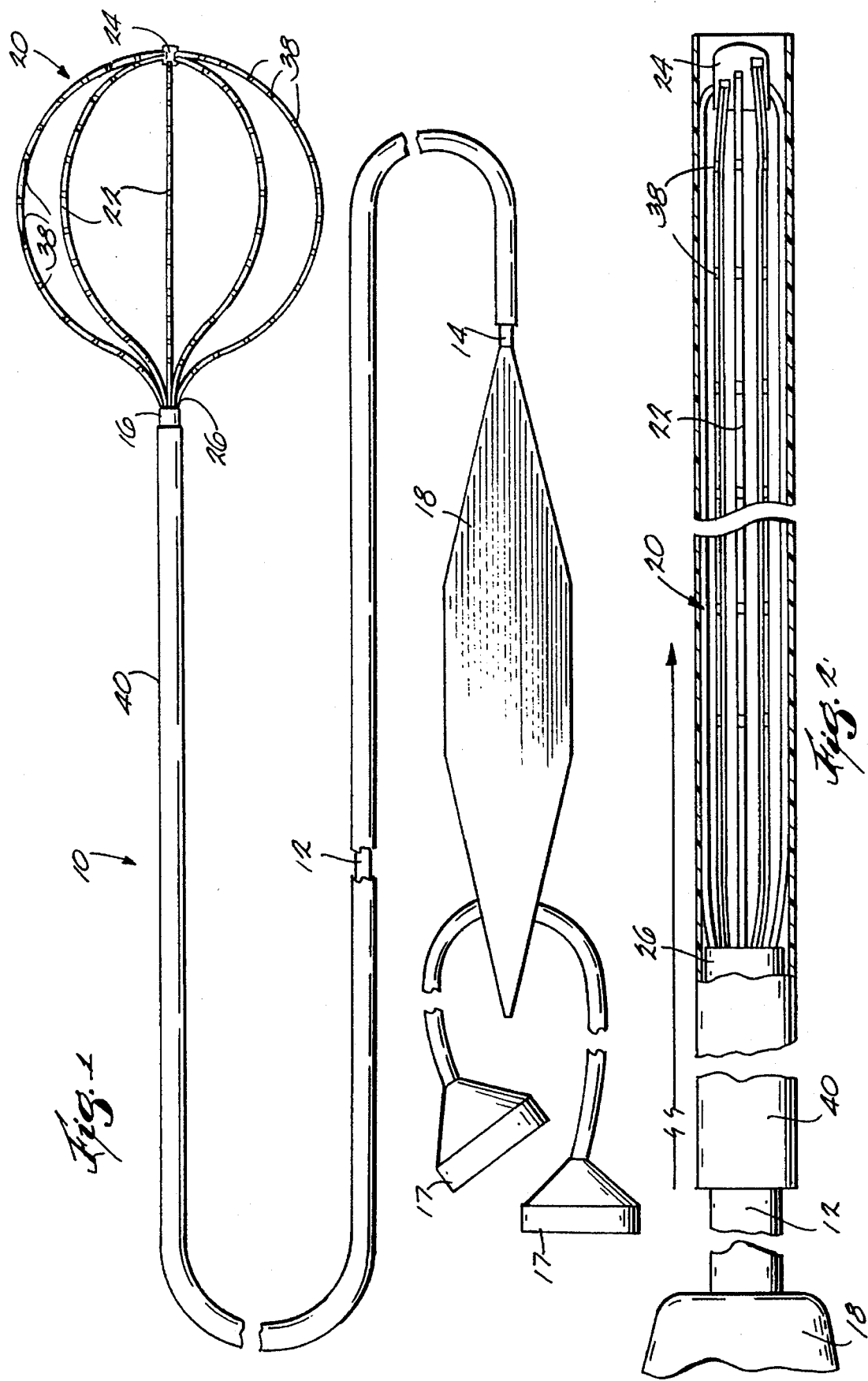

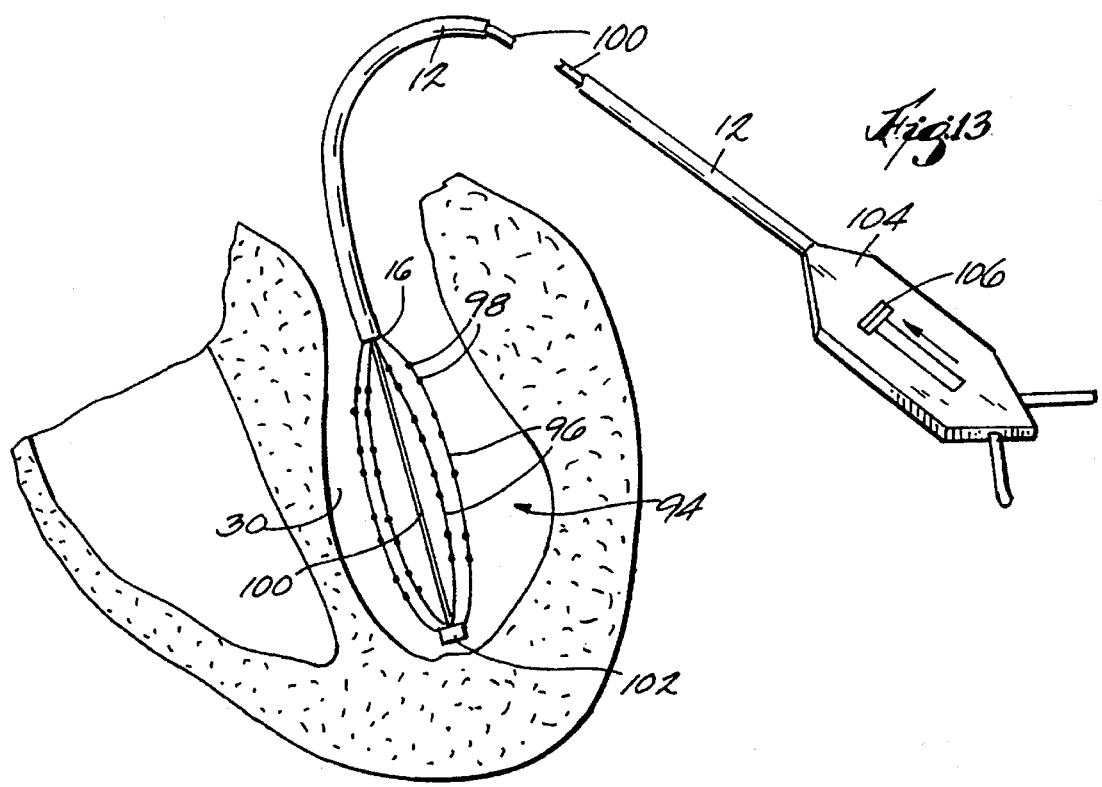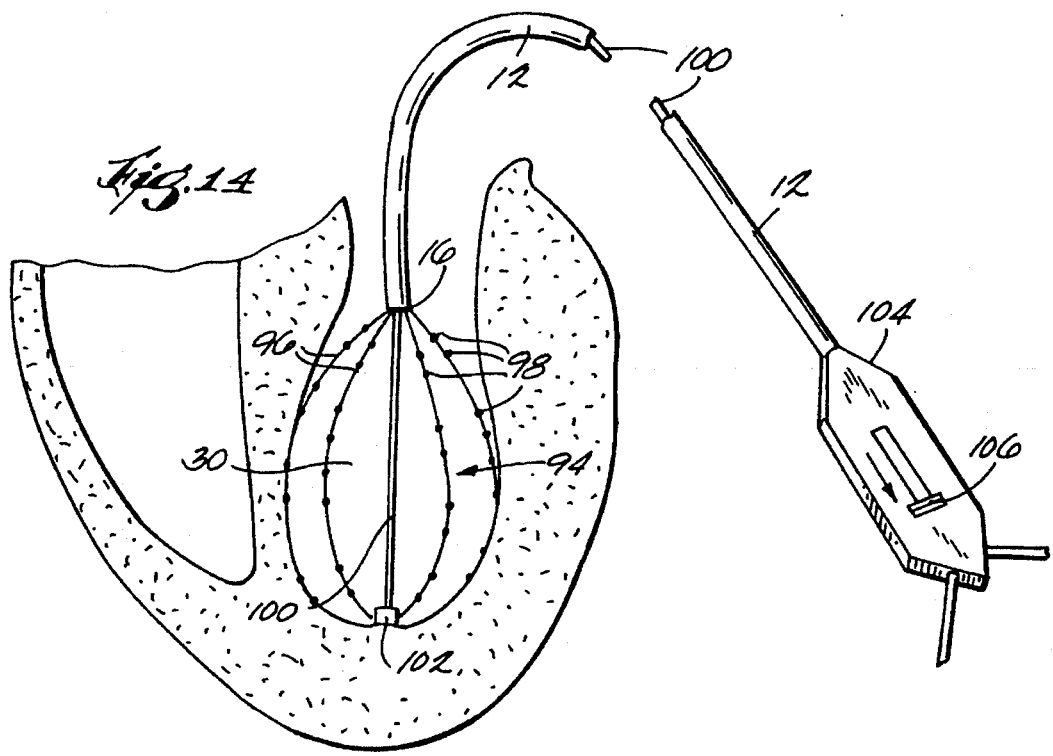

Fig. 15

SENSE DIFFERENTIAL IMPEDANCE FOR CONTACT

SENSE BLOOD PATH

```
┌─────────────────┐
│ URGE ELECTRODES │
│ INTO            │
│ BLOOD POOL      │
└────────┬────────┘
         │
┌────────▼────────┐
│ BEGIN           │
│ SENSING         │
│ CYCLE           │
│ n = 1           │
└────────┬────────┘
         │
┌────────▼──────────────┐
│ EMIT CURRENT          │◄──────┐
│ (BloodPathCurrent)    │       │
│ E(n)                  │       │
└────────┬──────────────┘       │
         │                      │
┌────────▼──────────────┐       │
│ MEASURE VOLTAGE       │       │
│ (BloodPathVoltage)    │       │
│ E(n) and EI           │       │
└────────┬──────────────┘       │
         │                      │
┌────────▼──────────────────┐   │
│ COMPUTE BLOOD PATH        │   │
│ IMPEDANCE                 │   │
│ (BloodPath Imp)           │   │
│ BloodPathVoltage/         │   │
│ BloodPathCurrent          │   │
└────────┬──────────────────┘   │
         │                      │
┌────────▼────────┐             │
│ n = n + 1       │             │
└────────┬────────┘             │
         │                      │
┌──NO────┴─────────────┐        │
│                      │        │
▼              ┌───────▼──────┐ │
              │ n = all      │─┘ NO
              │ electrodes?  │
              └───────┬──────┘
                      │ YES
              ┌───────▼──────────┐
              │ OBTAIN           │
              │ TISSUE PATH      │
              │ IMPEDANCES       │
              │ (GO TO FIG. 16)  │
              └──────────────────┘
```

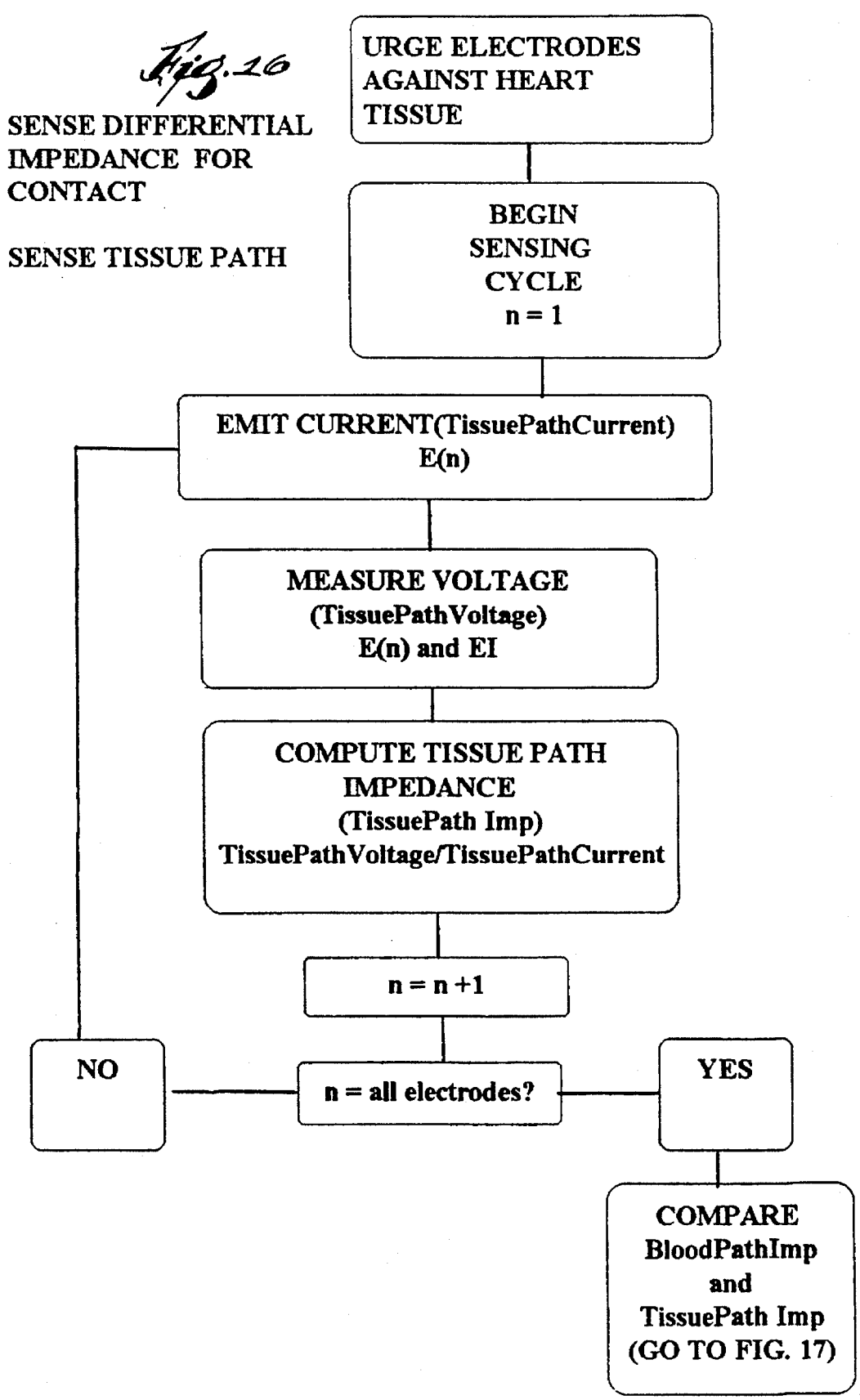

SENSE DIFFERENTIAL IMPEDANCE FOR CONTACT

COMPARE TISSUE PATH AND BLOOD PATH

SYSTEMS AND METHODS FOR POSITIONING MULTIPLE ELECTRODE STRUCTURES IN ELECTRICAL CONTACT WITH THE MYOCARDIUM

FIELD OF THE INVENTION

The invention relates to systems and methods for mapping and ablating the interior regions of the heart for treatment of cardiac conditions.

BACKGROUND OF THE INVENTION

Physicians make use of catheters today in medical procedures to gain access into interior regions of the body to ablate targeted tissue areas. It is important for the physician to be able to precisely locate the catheter and control its emission of energy within the body during tissue ablation procedures.

The need for precise control over the catheter is especially critical during procedures that ablate myocardial tissue from within the heart. These procedures, called electrophysiological therapy, are used to treat cardiac rhythm disturbances.

During these procedures, a physician steers a catheter through a main vein or artery into the interior region of the heart that is to be treated. The physician then further manipulates a steering mechanism to place the electrode carried on the distal tip of the catheter into direct contact with the endocardial tissue. The physician directs energy from the electrode through myocardial tissue either to an indifferent electrode (in a uni-polar electrode arrangement) or to an adjacent electrode (in a bi-polar electrode arrangement) to ablate the tissue and form a lesion.

Physicians examine the propagation of electrical impulses in heart tissue to locate aberrant conductive pathways and to identify foci, which are ablated. The techniques used to analyze these pathways and locate foci are commonly called "mapping."

Conventional cardiac tissue mapping techniques use multiple electrodes positioned in contact with epicardial heart tissue to obtain multiple electrograms. These conventional mapping techniques require invasive open heart surgical techniques to position the electrodes on the epicardial surface of the heart.

An alternative technique of introducing multiple electrode arrays into the heart through vein or arterial accesses to map myocardial tissue is known. Compared to conventional, open heart mapping techniques, endocardial mapping techniques, being comparatively non-invasive, hold great promise. Multiple electrogram signals obtained from within the heart can be externally processed to detect local electrical events and identify likely foci.

To achieve consistent, reliable foci identification rates, all electrodes in a multiple electrode array should be in intimate, electrical contact with heart tissue. With invasive, open heart techniques, multiple electrode contact on exposed epicardial surfaces can be visually confirmed directly by the physician. However, with comparatively non-invasive endocardial mapping techniques, confirming multiple electrode contact within the beating heart can be problematic.

There is the need to provide simple, yet reliable ways of assuring that the electrodes of an endocardial multiple electrode structure are in intimate, electrical contact with tissue within the heart.

SUMMARY OF THE INVENTION

This invention has as its principal objective the realization of safe and efficacious endocardial mapping techniques.

One aspect of the invention provides a system and related method for evaluating electrical contact between the myocardium and at least two spaced apart electrodes in the heart. The system and method generate a first unitary contact-indicating output indicating the presence or absence of electrical contact between the myocardium and one of the electrodes. The system and method also generate a second unitary contact-indicating output indicating the presence or absence of electrical contact between the myocardium and the other electrode.

In a preferred embodiment, the system and method correlate the electrode-specific unitary contact-indicating outputs to generate a compound contact-indicating output. The compound output indicates the aggregate of the electrical contact between the myocardium and multiple electrodes in a multiple electrode array.

In one implementation, the system and method sense electrical contact by emitting through the electrodes an electrical signal that does not activate the myocardium. In a preferred arrangement, the system and method acquire a tissue impedance measurement based upon this emission.

In a preferred implementation, the system and method sense electrical contact by emitting through the electrodes an electrical signal that activates the myocardium, like a pacing pulse. In this implementation, the system and method acquire an electrogram based upon this signal emission.

In a preferred implementation, the system and method evaluate electrical contact for a multiple electrode array that comprises electrodes supported on circumferentially spaced splines. The system and method electrically evaluate electrical contact to obtain a unitary contact-indicating output for at least one electrode on each spline. The system and method also correlate these unitary contact-indications to obtain a compound contact-indication, indicating the aggregate electrical contact between the myocardium and the multiple electrode array.

Another aspect of the invention electrically evaluates electrical contact between the myocardium and an electrode inside the heart by emitting electrical energy into the myocardium through the electrode. The system and method that embody this aspect of the invention detect at least one selected signal resulting from the emission of electrical energy by the electrode. The selected signal varies with electrical contact between the electrode and the myocardium to differentiate between electrical contact and the absence of electrical contact. The system and method process the acquired signal by comparing it to an expected signal. The system and method generate a contact-indicating output for the electrode based upon the comparison. The contact-confirm output indicates the presence of electrical contact between the electrode and the myocardium in the form of a contact-confirm signal, and a contactcontrary output indicates the absence of such contact.

Other features and advantages of the inventions are set forth in the following Description and Drawings, as well as in the appended Claims.

BRIEF DESCRIPTION OF THE DRAWINGS

FIGS. 1 and 2 are plan views of an endocardial mapping probe having a collapsible multiple electrode structure whose electrical contact with the myocardium can be evaluated using a contact sensing module that embodies the features of the invention;

FIG. 13 shows in somewhat diagrammatic form an alternative embodiment of a collapsible endocardial multiple electrode structure deployed in the left ventricle, being shown in a partially collapsed condition for urging electrical contact mostly with the blood pool;

FIG. 14 shows in somewhat diagrammatic form the alternative embodiment shown in FIG. 13, with the multiple electrode structure in an expanded condition for urging electrical contact mostly with the myocardium;

FIG. 15 is a flow chart showing the operation of a contact sensing module usable in association with the multiple electrode structure shown in FIGS. 13 and 14 with the structure in its partially collapsed condition for sensing blood path impedance;

FIG. 16 is a flow chart showing the operation of a contact sensing module usable in association with the multiple electrode structure shown in FIGS. 13 and 14 with the structure in its expanded condition for sensing tissue path impedance.

Figure 3:
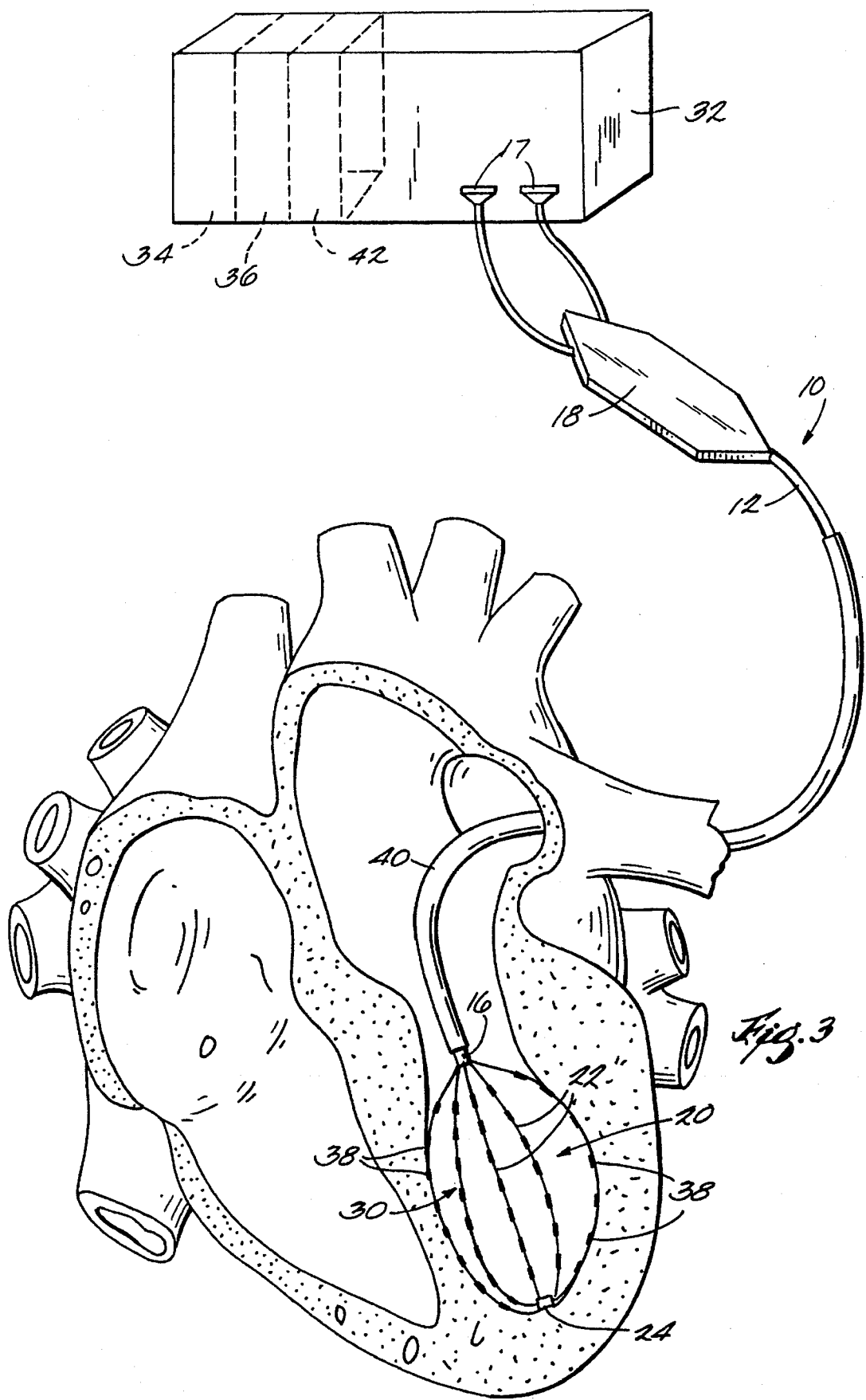
FIG. 3 is a somewhat diagrammatic view of the mapping probe shown in FIGS. 1 and 2 deployed in the left ventricle of the heart and electrically coupled to a process controller that includes a contact sensing module that embodies the features of the invention.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

FIG. 1 shows an endocardial mapping probe 10. The probe 10 comprises a flexible catheter tube 12 with a proximal end 14 and a distal end 16. The proximal end 14 carries an attached handle 18. The distal end 16 carries a multiple electrode support assembly 20.

The multiple electrode support assembly 20 comprises an array of flexible spline elements 22 assembled to form a three dimensional structure. The far ends of the spline elements 22 radiate from a distal hub 24. The near ends of the spline elements 22 are affixed to a base 26, which the distal end 16 of the catheter tube 12 carries.

Preferably, the spline elements 22 comprise thin, rectilinear strips of resilient metal or plastic material. Still, other cross sectional configurations can be used.

The support assembly 20 retains the spline elements 22 in a circumferentially spaced array. In the illustrated embodiment, the array takes the shape of a three dimensional basket structure. Of course, the resulting structure can assume other shapes.

The spline elements 22 carry an array of electrodes 38. Signal wires (not shown) electrically coupled to the electrodes pass along the guide tube 12 and connect to connectors 17 carried outside the handle 18.

In the illustrated and preferred embodiment, the probe 10 includes an outer sheath 40 carried about the catheter tube 12. As FIG. 2 best shows, the sheath 40 has an inner diameter that is greater than the outer diameter of the catheter tube 12. As a result, the sheath 40 slides along the catheter tube 12 (as the arrows in FIG. 2 show).

As FIG. 2 shows, forward movement advances the slidable sheath 40 over the support assembly 20. In this position, the slidable sheath 40 compresses and collapses the support assembly 20 for introduction through a vein or artery to the intended treatment site within the body.

As FIG. 1 shows, rearward movement retracts the slidable sheath 40 away from the support assembly 20. This removes the compression force. The freed support assembly 20 opens and assumes its three dimensional shape inside a heart chamber.

The electrode support assembly 20 can be assembled in different ways. Representative support assemblies are shown in co-pending U.S. patent application Ser. No. 08/206,414, filed Mar. 4, 1994, entitled "Multiple Electrode Support Structures," which is incorporated herein by reference.

FIG. 3 shows the support assembly 20 deployed and ready for use inside a chamber 30 in the human heart. FIG. 3 generally shows the support assembly 20 deployed in the left ventricle of the heart. Of course, the assembly 20 can be deployed in other regions of the heart, too. It should also be noted that the heart shown in the Figures is not anatomically accurate. The Figures show the heart in diagrammatic form to demonstrate the features of the invention.

As FIG. 3 shows, when deployed within the heart, the circumferentially spaced splines 22 make contact with circumferentially spaced regions of the endocardium.

As FIG. 3 also shows, the connectors 17 plug into a processing system 32. The system 32 includes an on board signal processing module 34 that receives and processes diagnostic signals from the multiple electrodes 38 on the assembly 20. The output of the module 34 helps the physician in identifying appropriate ablation sites within the heart. The type of signals that the module 34 receives and processes can vary, according to the choice of the physician.

For example, the physician can condition the module 34 to take multiple, sequential measurements of the transmission of electrical current by heart tissue to obtain tissue resistivity measurements. The processing of tissue resistivity signals to identify appropriate ablation sites is disclosed in co-pending U.S. patent application Ser. No. 08/197,236, filed Jan. 28, 1994, and entitled "Systems and Methods for Matching Electrical Characteristics and Propagation Velocities in Cardiac Tissue to Locate Potential Ablation Sites."

Alternatively, or in conjunction with tissue resistivity measurements, the physician can condition the module 34 to acquire and process electrograms in a conventional fashion. The module 34 processes the electrogram information to map the conduction of electrical impulses in the myocardium.

Furthermore, if desired, the physician can condition one or more of the electrodes 38 to emit a therapeutic signal into the myocardium. For example, the physician can condition selected electrodes 38 to emit radio-frequency energy to ablate myocardial tissue. Alternatively, a separate ablation probe (not shown) can be deployed for this purpose.

Regardless of the particular type of signal that is processed, the support assembly 20 should be oriented in the heart chamber 30 to hold all or substantially all electrodes 38 in electrical contact the myocardium. According to the invention, the controller 32 includes a tissue contact sensing module 36. The contact sensing module 36 evaluates electrical contact between the myocardium and the multiple electrode array inside the heart.

As will be described in greater detail later, the contact sensing module 36 electrically senses electrical contact between the myocardium and at least one electrode 38 on spaced apart spline elements 22. The module 36 generates a unitary contact-indicating output for the energy emitting electrodes 38. The unitary output indicates the presence or absence of the electrical contact between a particular electrode and the myocardium.

In the illustrated and preferred embodiment, the module 36 also correlates the electrode-specific unitary contact-indicating outputs to generate a compound contact-indicating output. The compound output indicates the aggregate electrical contact between the myocardium and the multiple electrode array.

In the preferred embodiment the module 36 electrically senses electrical contact by emitting from one or more of the electrodes 38 an electrical signal that activates the myocardium. In this embodiment, the module 36 ascertains electrical contact by detecting electrograms.

In another embodiment, the module 36 electrically senses electrical contact by emitting from one or more of the electrodes 38 an electrical signal that does not activate the myocardium. In this arrangement, the module 36 ascertains electrical contact by measuring tissue impedance.

I. Pace-Locate Module

Figure 4:
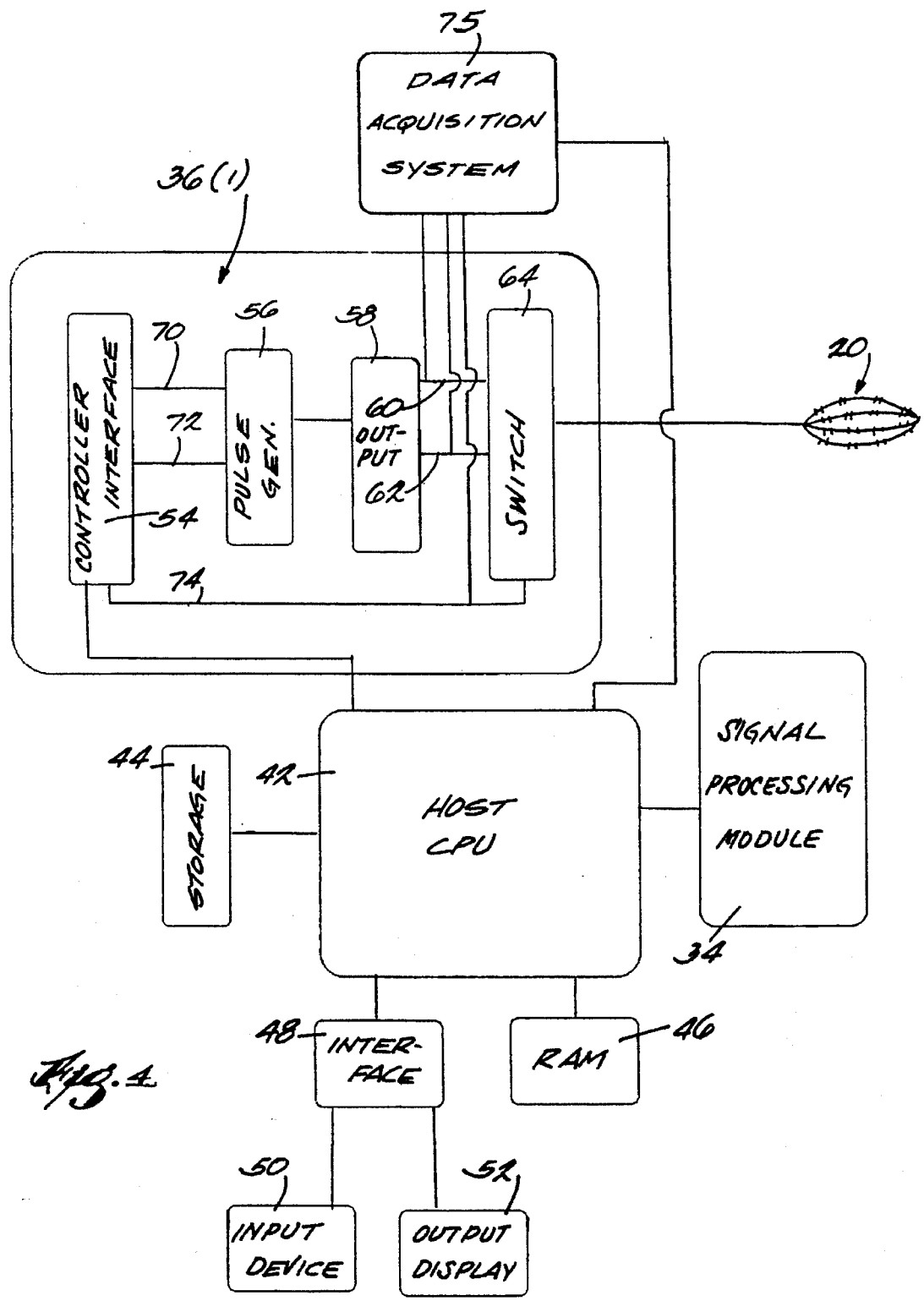
FIG. 4 is a schematic view of a preferred implementation of a contact sensing module that embodies the features of the invention by sensing electrical contact with the myocardium using pacing signals.
Figure 5:
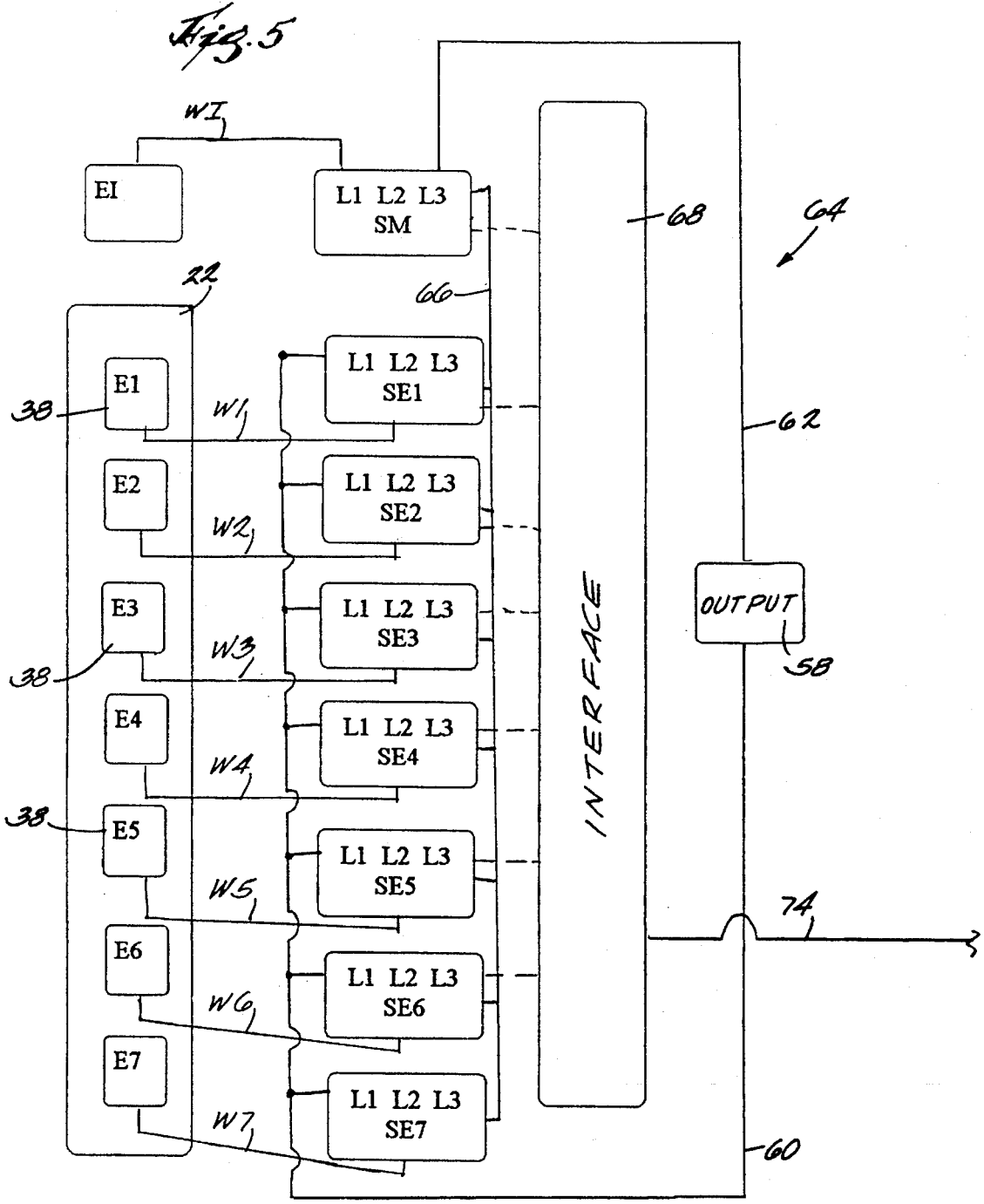
FIGS. 5 and 6 are schematic views of a switching device used in association with the contact sensing module shown in FIG. 4.
Figure 6:
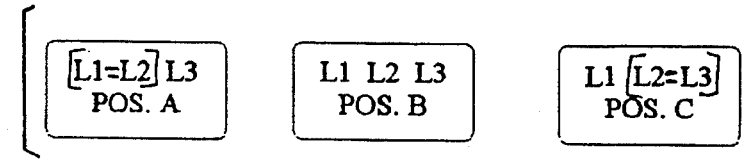

FIGS. 4 to 6 show a preferred implementation of the contact sensing module (designated 36(1)) and the associated processing system 32.

In this implementation, the module 36(1) generates pacing signals to evaluate the quality of electrical contact between the electrodes 38 and the myocardium. This sensing information is preferably obtained by pacing at the end of diastole, at the stage of the cardiac cycle when the heart is at its maximum relaxation.

In this implementation (see FIG. 4), the processing system 32 includes a host central processing unit (CPU) 42 (as FIG. 3 also shows). The CPU 42 communicates with a mass storage device 44 and an extended static RAM block 46. A user interactive interface 48 also communicates with the CPU As FIG. 4 shows, the interactive user interface 48 includes an input device 50 (for example, a key board or mouse) and an output display device 52 (for example, a graphics display monitor or CRT).

The CPU 42 communicates with both the signal processing module 34 and the contact sensing module 36(1). The CPU 42 coordinates the control functions for the modules 34 and 36(1).

In the illustrated and preferred implementation (as FIG. 4 shows), the contact sensing module 36(1) includes a controller interface 54 coupled to the host processor 42. The controller interface 54 is also coupled to a pulse generator 56 and an output stage 58.

The output stage 58 is electrically coupled by supply path 60 and return path 62 to a switching element 64. The configuration of the switching element 64 can vary. FIG. 5 diagrammatically shows one preferred arrangement.

FIG. 5 shows for illustration purposes a spline 22 with seven adjacent electrodes 38, designated E1 to E7. Each electrode E1 to E7 is electrically coupled to its own signal wire, designated W1 to W7. An indifferent electrode, designated EI in FIG. 5, is also electrically coupled to its own signal wire WI. The indifferent electrode EI is preferably an electrode in the blood pool. However, the indifferent electrode EI can be formed by other means. For example, it can also be a conventional patch electrode attached on the outside of the patient's body.

In this arrangement, the switching element 64 includes an electronic switch $S_M$ and electronic switches $S_{E1}$ to $S_{E7}$ that electrically couple the pacing output stage 58 to the signal wires W1 to W7. The switch $S_M$ governs the overall operating mode of the electrodes E1 to E7 (i.e., unipolar or bipolar). The switches $S_{E1}$ to $S_{E7}$ govern the electrical conduction pattern of the electrodes E1 to E7.

The switches $S_M$ and $S_{E1\ to\ E7}$ are electrically coupled to the output stage 58 of the pulse generator 56 through the lines 60 and 62. The supply line 60 of the output stage 58 is electrically coupled to the leads L1 of the switches $S_{E1\ to\ E7}$. The return line 62 of the output stage 58 is electrically coupled to the center lead L2 of the mode selection switch $S_M$. A connector 66 electrically couples the leads L3 of the switches $S_M$ and $S_{E1\ to\ E7}$.

The center leads L2 of the selecting switches $S_{E1\ to\ E7}$ are directly electrically coupled to the signal wires W1 to W7 serving the electrodes E1 to E7, so that one switch $S_{E(N)}$ serves only one electrode $E_{(N)}$.

The lead L1 of the switch $S_M$ is directly electrically coupled to the signal wire WI serving the indifferent electrode EI.

An interface 68 electronically sets the switches $S_M$ and $S_{E1\ to\ E7}$ among three positions, designated A, B, and C in FIG. 6.

As FIG. 6 shows, Position A electrically couples leads L1 and L2 of the associated switch. Position C electrically couples leads L2 and L3 of the associated switch. Position B electrically isolates both leads L1 and L3 from lead L2 of the associated switch.

Position B is an electrically OFF position. Positions A and B are electrically ON positions.

By setting switch $S_M$ in Position B, the interface 68 electronically inactivates the switching network 64.

By setting switch $S_M$ in Position A, the interface 68 electronically configures the switching element for operation in the unipolar mode. The center lead L2 of switch $S_M$ is coupled to lead L1, electronically coupling the indifferent electrode EI to the return 62 of the pulse output stage 58. This configures the indifferent electrode EI as a return path for current.

With switch $S_M$ set in Position A, the interface 68 electronically selectively configures each individual electrode E1 to E7 to emit current by sequentially setting the associated switch $S_{E1\ to\ E7}$ in Position A. When the selected electrode E1 to E7 is so configured, it is electronically coupled to the supply 60 of the pulse output stage 58 and emits current. The indifferent electrode EI receives the current sequentially emitted by the selected electrode E1 to E7.

By setting switch $S_M$ in Position C, the interface 68 electronically isolates the indifferent electrode EI from the electrodes E1 to E7. This configures the switching element for operation in the bipolar mode.

With switch $S_M$ set in Position C, the interface 68 can electronically alter the polarity of adjacent electrodes E1 to E7, choosing among current source, current sink, or neither.

By setting the selected switch $S_{E1\ to\ E7}$ in Position A, the interface 68 electronically configures the associated electrode E1 to E7 to be a current source. By setting the selected switch $S_{E1\ to\ E7}$ in Position C, the interface 68 electronically configures the associated electrode E1 to E7 to be a current sink. By setting the selected switch $S_{E1\ to\ E7}$ in Position B, the interface 68 electronically turns off the associated electrode E1 to E7.

The controller interface 54 of the module 36(1) includes control buses 70, 72, and 74. Bus 70 conveys pulse period control signals to the pulse generator 56. Bus 72 conveys pulse amplitude control signals to the pulse generator 56. Bus 74 constitutes the control bus path for the switching element 64 by the means of interface 68.

When used to pace the heart, the switching element 64 distributes pacing signals generated by the pulse generator 56 to selected basket electrodes 38. The pacing sequence is governed through the interface 54 by the host processor 42.

When emitted by a selected electrode 38 in electrical contact with viable myocardium, the pacing signal depolarizes myocardial tissue at the site of the selected electrode 38. Since the intensity of the electric field generated by the pacing signal decreases with the square of the distance from the emitting electrode 38, the pacing signal will not be effective unless the emitting electrode 38 is very near or in intimate contact with viable myocardium.

The basket electrodes 38 will sense signals as the depolarization front generated by the pacing signal reaches them. These signals are passed back through the switching element 64 and the data acquisition system 75 to the host processor 42 for analysis according to prescribed criteria, which will be described in greater detail later. The analysis generates contact-indicating output. The contact-indicating output reflects the quality of electrical contact that exists between the myocardium and one or more electrodes 38 on the support assembly 20.

In the illustrated and preferred implementation, the module 36(1) operates in two modes. In the first mode, the module 36(1) operates to establish a reliable electrode pacing site by assessing the quality of electrical contact of a single, selected electrode 38 on the support assembly 20 (which will also be called a "unitary contact-indicating output."). In the second mode, the module 36(1) generates pacing signals in succession from multiple electrode pacing sites to generate the contact-indicating output, which assesses the quality of electrical contact for a composite of all the electrodes on the support assembly 20 (which will also be called a "compound contact-indicating output").

(i) Mode 1: Establishing Unitary Contact

Figure 7:
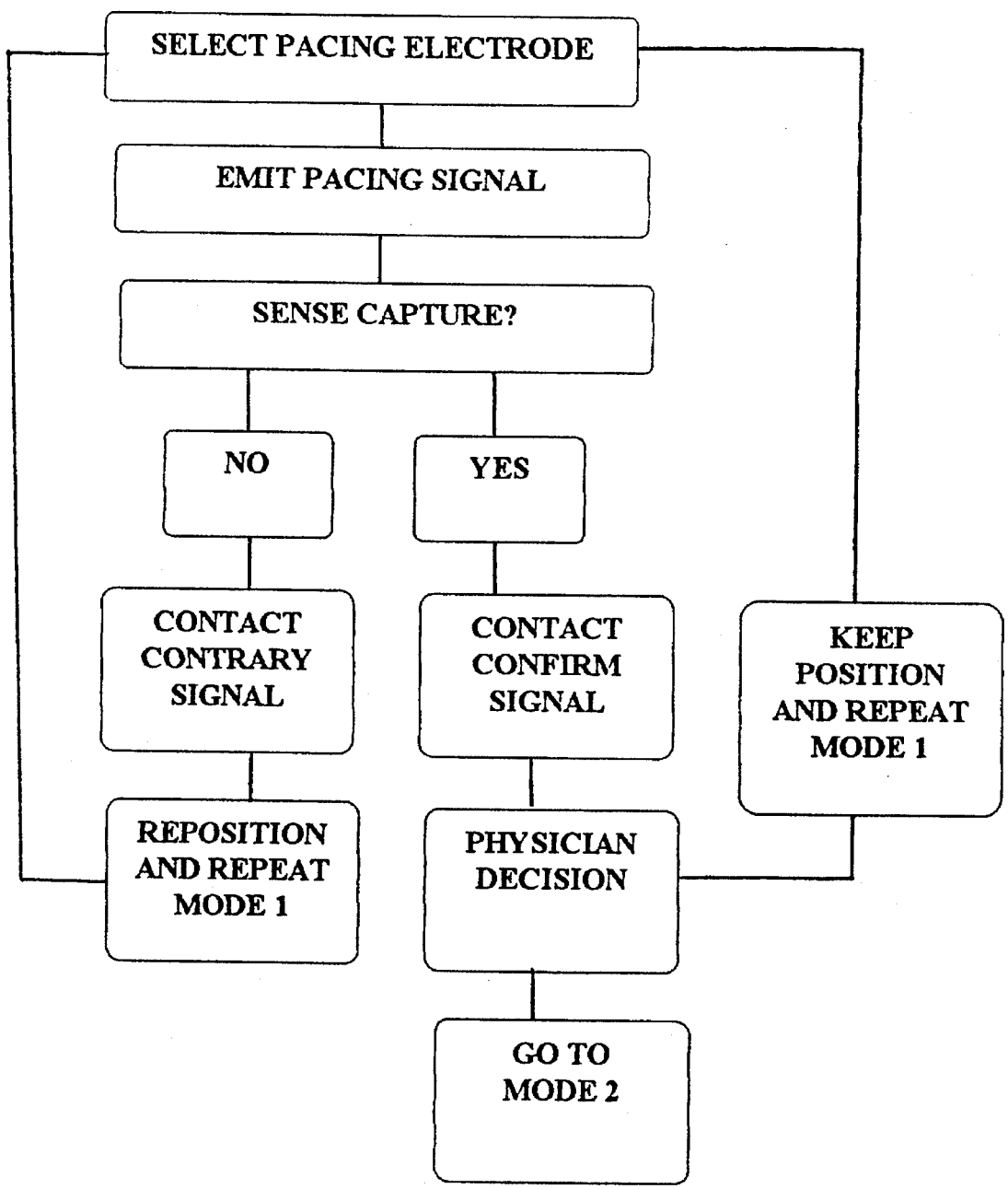
FIG. 7 is a flow chart showing the operation of the contact sensing module shown in FIG. 4 in Mode 1.

In Mode 1 (see FIG. 7), the CPU 42 selects one electrode 38 on the support structure 20. Through the controller interface 54, the CPU 42 causes the pulse generator 56 to generate a pacing signal through the switching element 64 to the selected electrode.

In Mode 1, the pacing signal must provide enough voltage or current to the selected electrode to locally stimulate the myocardium. Still, the pacing signal should not be large enough to field stimulate the myocardium at a distance greater than about 2 mm. In the preferred implementation, it is believed that the pacing signal should be about 3 milliamps (3 Volts), with a pulse width of about 0.5 msec.

By analyzing signals received back through the switching element 64 from at least one electrode on the support assembly 20, the CPU 42 confirms capture; that is, the CPU 42 confirms that a depolarization wavefront emanated from the selected electrode in response to the pacing signal. In the preferred implementation, the CPU 42 requires all or at least a significant number of electrodes spaced from the selected electrode to sense capture. The greater the number of sensing electrodes used to sense capture, the more reliable the overall output will be.

Upon sensing capture at the selected electrode, the CPU 42 generates a unitary contact-confirm signal. The unitary contact-confirm signal indicates that the selected electrode is in sufficient electrical contact with viable myocardium. The CPU 42 then automatically switches to the module 36(1) to Mode 2 operation.

In the preferred implementation of Mode 1, multiple pacing signals are sent to the selected electrode and multiple captures are confirmed. This confirms that the module 36(1) is working reliably, and that the electrical stimulus of the pacing signal is large enough to proceed to Mode 2 operation.

If signals received back through the switching element 64 from at least one electrode on the support assembly 20, do not confirm capture, the CPU 42 generates a unitary contact-contrary signal. The unitary contact-contrary signal indicates either (i) the selected electrode is not in sufficient electrical contact with the myocardium, or (ii) that the myocardium that the selected electrode contacts is not viable. The unitary contact-contrary signal advises the physician to relocate the support structure 20 and repeat Mode 1 until a unitary contact-confirm signal is received or he/she decides that the myocardium is not viable.

(ii) Mode 2: Establishing Compound Contact

Figure 8:
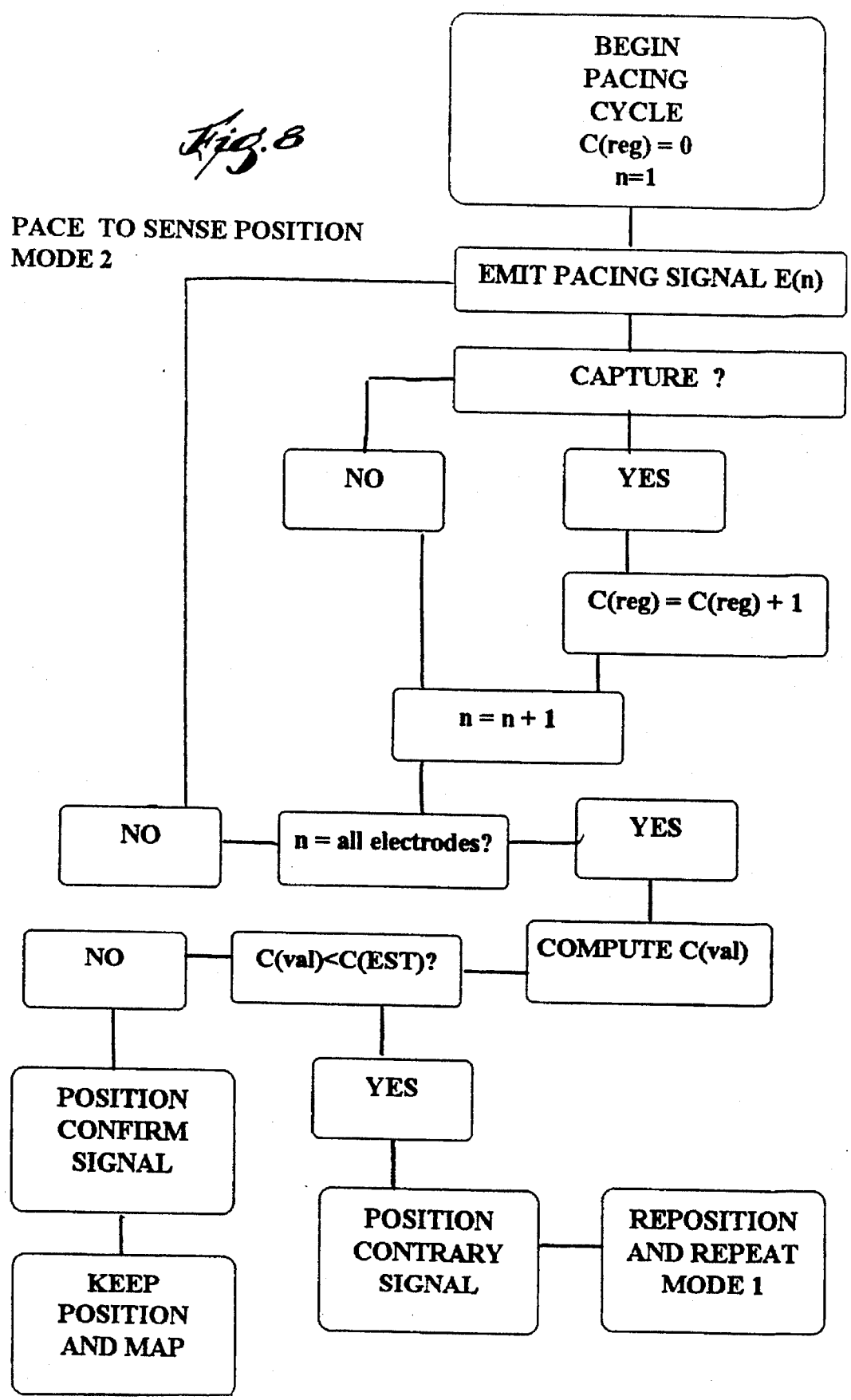
FIG. 8 is a flow chart showing the operation of the contact sensing module shown in FIG. 4 in Mode 2.

Upon entering Mode 2 (see FIG. 8), the CPU 42 causes the controller interface 54 to perform a prescribed pacing cycle. During the pacing cycle, the switching element 64 sends a pacing signal in succession to a selected number of electrodes 38. In the preferred implementation of Mode 2, every electrode on the support structure receives at least one pacing signal during the pacing cycle.

The pacing rate must be faster than the baseline heart beat (that is, typically greater than about 70 beats per minute). Preferably, the pacing rate should be at least 20% larger than the baseline heart beat (that is, typically greater than 84 beats per minute).

For example, a pacing rate of 120 pacing signals per minute could be selected. Given 60 pacing signals during each pacing cycle (for a support assembly 20 having 60 electrodes), this selected pacing rate would require 30 seconds to complete one pacing cycle.

The CPU 42 registers the number of captures sensed during the pacing cycle. The CPU 42 then evaluates, for each pacing cycle, the number of registered captures against predetermined criteria. Based upon this evaluation, the signal processing system generates the compound contact-indicating output.

In the preferred implementation, the CPU 42 compares, for each pacing cycle, the number of registered captures to the maximum possible number of captures. From this comparison, the signal processing system creates a contact value $C_{VAL}$, which is computed as follows:

$$C_{VAL} = \frac{C_{REG}}{C_{MAX}} \times 100$$

where $C_{REG}$ is the actual number of registered captures during the pacing cycle, and $C_{MAX}$ is the maximum number of captures possible during the pacing cycle, which corresponds to the number pacing signals generated during the pacing cycle.

In this implementation, the CPU 42 compares the contact value $C_{VAL}$ to a predetermined value $C_{EST}$ to generate the compound contact-indicating output.

If the contact value $C_{VAL}$ equals or exceeds the predetermined value $C_{EST}$, the CPU 42 generates through the output 52 a compound contact-confirming signal. The compound contact-confirming signal indicates to the physician that the electrodes 38 on the support structure 20 are in sufficient contact with the myocardium to perform a reliable mapping procedure.

If the contact value $C_{VAL}$ lies below the predetermined value $C_{EST}$, the CPU 42 generates through the output 52 a compound contact-contrary signal. The compound contact-contrary signal indicates to the physician that the electrodes 38 on the support structure 20 are not in sufficient electrical contact with the myocardium to perform a reliable mapping procedure. The combined contact-contrary signal suggests that the physician should relocate the support assembly and repeat Mode 1.

In either situation, in Mode 2 operation, the module 36(1) allows the physician to generate another pacing cycle to confirm the compound contact-indicating output.

The predetermined capture value $C_{EST}$ can vary according to the physiology of the patient, the structure of the electrode support assembly, and the medical judgement of the physician. For example, $C_{EST}$ for a patient having entirely viable myocardium can be larger than for a patient having damaged heart tissue. The $C_{EST}$ for an assembly 20 having a larger number of electrodes 38 can be smaller than for an assembly 20 having a smaller number of electrodes 38. The medical judgement of one physician may require a larger $C_{EST}$ than another physician.

Taking these variables into consideration, it is believed that an acceptable $C_{EST}$ lies in the range of about 50 to 100. A realistic target for $C_{EST}$ is believed to lie at or above 85 for most procedures.

In the preferred implementation, pacing is accomplished by operating the electrodes 38 in a uni-polar configuration (that is, by setting switch $S_M$ in Position A in FIG. 5). In this configuration, an external indifferent electrode EI serves as the return path for the pacing signal.

In an alternative implementation, the pacing could be accomplished by operating the electrodes 38 in a bi-polar configuration (that, by setting switch $S_M$ in Position C in FIG. 5). In this configuration, the pacing signal is generated between spaced apart pairs of electrodes 38 on the support assembly 20 using bipolar pacing techniques. Preferably, one of the electrodes 38 of the bipolar pair is known not to be in electrical contact with viable myocardium. Pacing artifacts are reduced using bipolar pacing.

Once the module generates a compound contact-confirming signal during Mode 2, the physician can cause the process controller 32 to switch to the signal processing module 34 and proceed with the intended mapping process.

Once a satisfactory compound contact-confirming signal is received, the CPU 42 can also specifically identify the electrode sites where capture is sensed and not sensed. By operating the module 36(1) in Mode 2 through successive pacing cycles, the CPU 42 can generate electrode-specific information. For example, the CPU 42 can process historical information obtained during successive pacing cycles to identify locations where capture is consistently not sensed. By generating an output identifying those electrode locations where capture is consistently not sensed, the CPU 42 provides the physician with information that, on a gross scale, indicates where regions of nonviable (i.e., infarcted) myocardium exist.

II. Tissue Impedance-Locate Module

Figure 9:
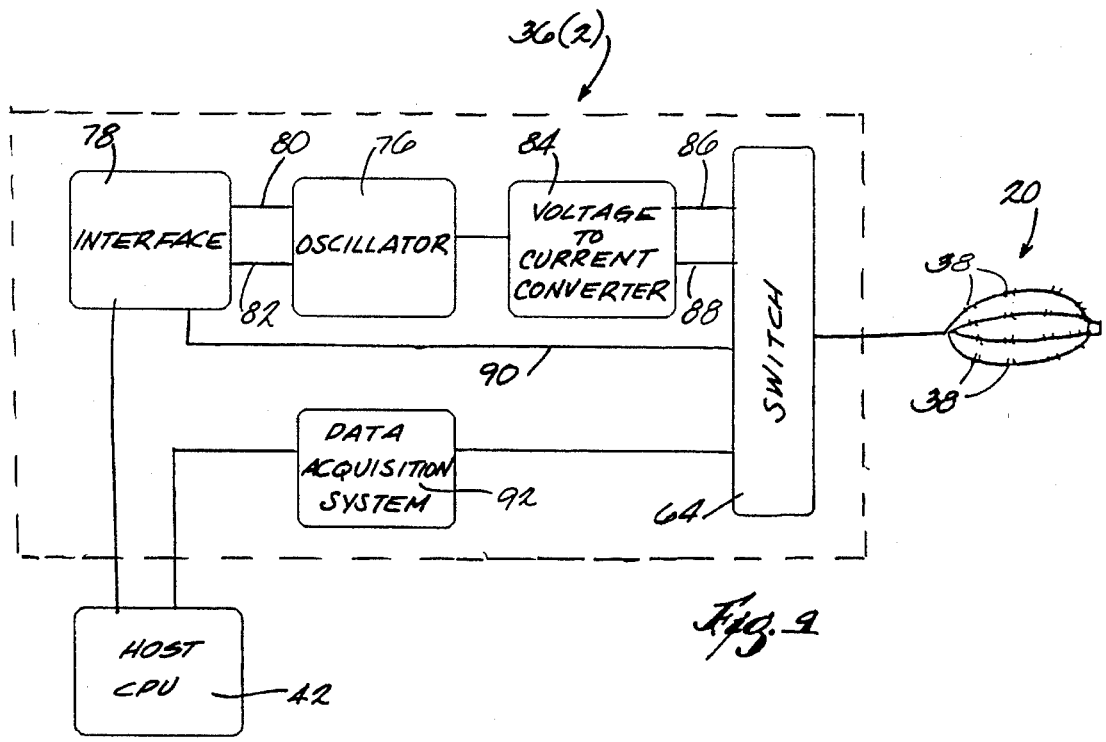
FIG. 9 is a schematic view of an alternative implementation of a contact sensing module that embodies the features of the invention by sensing electrical contact with the myocardium using tissue impedance measurements.

FIG. 9 shows an alternative implementation of the contact sensing module (designated 36(2)). In this embodiment, the module 36(2) derives contact-indicating information by measuring tissue impedance.

The module 36(2) offers the physician the capability of sensing contact throughout the cardiac cycle, systole and diastole. The module 36(2) also simplifies sensing contact at each individual electrode site.

As FIG. 9 shows, the module 36(2) includes an oscillator 76 that generates a sinusoidal voltage signal. An associated interface 78 has a bus 80 that controls the frequency of the output voltage signal and a bus 82 that controls the amplitude of the output voltage signal. The interface 78, in turn, is programmed by the host CPU 42, already described.

The oscillator 76 has as an output stage that includes a voltage-to-current converter 84. In conventional fashion, the converter 84 converts the sinusoidal voltage signal to current.

In the illustrated and preferred embodiment, the transmitted current has an amplitude of about 0.1 milliamps to 5.0 milliamps. The lower range of the current amplitude is selected to be high enough to overcome the influence of the double layer at the tissue-electrode interface on the impedance measurement. The high range of the current amplitude is selected to avoid the induction of fibrillation.

The current has a frequency in a range of about 5 to 50 kHz. The range is selected to avoid the induction of fibrillation, as well as provide contrast between infarcted tissue and healthy tissue. The output of the converter 84 can comprise a constant current with a constant frequency within the above range. Alternatively, the interface 78 can control the modulation of the frequency of the current signal within the prescribed range.

The current output of the module 36(2) is supplied to the basket electrodes 38 via supply path 86 through the switching element 64, already described and shown in FIG. 5. The interface 78 electronically configures the switching element 64 to direct current in succession to selected basket electrodes 38 through their associated signal wires in a unipolar mode (that is, with switch $S_M$ in Position A). When operated in a unipolar mode, the current return path 88 to the switch element 64 is provided by the indifferent electrode EI attached to the patient. Line 90 constitutes the control bus for the switching element 64.

The module 36(2) includes a data acquisition system 92. While current is emitted by each selected basket electrode 38, the system 92 senses the voltage in the tissue path lying between the selected electrode 38 and the indifferent electrode EI. Based upon the data acquired by the system 92, the host processor 42 computes the impedance of the path (in ohms) lying between the electrodes.

The measured path impedance can be directly correlated to electrode contact with tissue. A relatively high impedance value indicates electrical contact with healthy myocardium, while a relatively low impedance value indicates either a lack of electrical contact or the presence of infarcted myocardium in the path.

Preliminary tests indicate that for good contact the impedance with respect to a 40 cm² patch electrode on the back of the patient is about 200 ohms. For poor contact the impedance is about 125 ohms. Other values can be obtained for different electrode geometries.

The CPU 42 analyzes the computed impedance values according to prescribed criteria. Based upon this comparison, the CPU 42 generates a contact-indicating output. The contact-indicating output reflects the amount of electrical contact that exists between the myocardium and one or more electrodes 28 on the support assembly 20.

Figure 10:
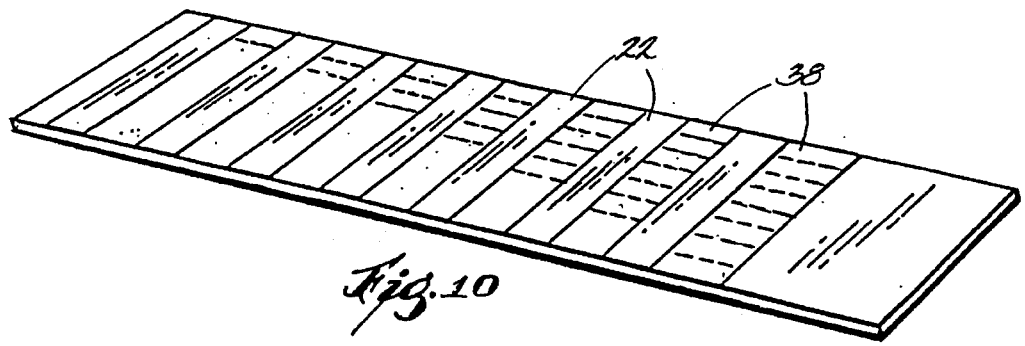
FIG. 10 is an enlarged perspective view of a part of the multiple electrode assembly usable in association with the contact sensing module shown in FIG. 9.

In this implementation (as FIG. 10 shows), the electrodes 38 are mounted to each spline 22 to maximize surface contact with endocardial tissue, while at the same time minimizing exposure to the surrounding blood pool. Incidental exposure of the electrodes 38 to blood while in contact with heart tissue introduces an unwanted artifact to tissue impedance measurement, because the resistivity of blood is about three times lower than the resistivity of heart tissue. This artifact can skew the impedance measurement to a lower value, thereby reducing the desired contrast between contact-confirm and contact-contrary signals.

In the illustrated embodiment, the electrodes 38 are made of platinum or gold plated stainless steel bands affixed to only one side of the rectilinear splines 22. This is the side of the spline 22 that, in use, contacts endocardial tissue. The opposite surface of the splines 22 (which, in use, contacts the blood pool) is free of electrodes.

It is believed that no more than 20% of the electrode surface should be exposed to the blood pool during use Preferable, less than 5% of the electrode should be so exposed during use.

(i) Determine Absolute Tissue Contact

Figure 11:
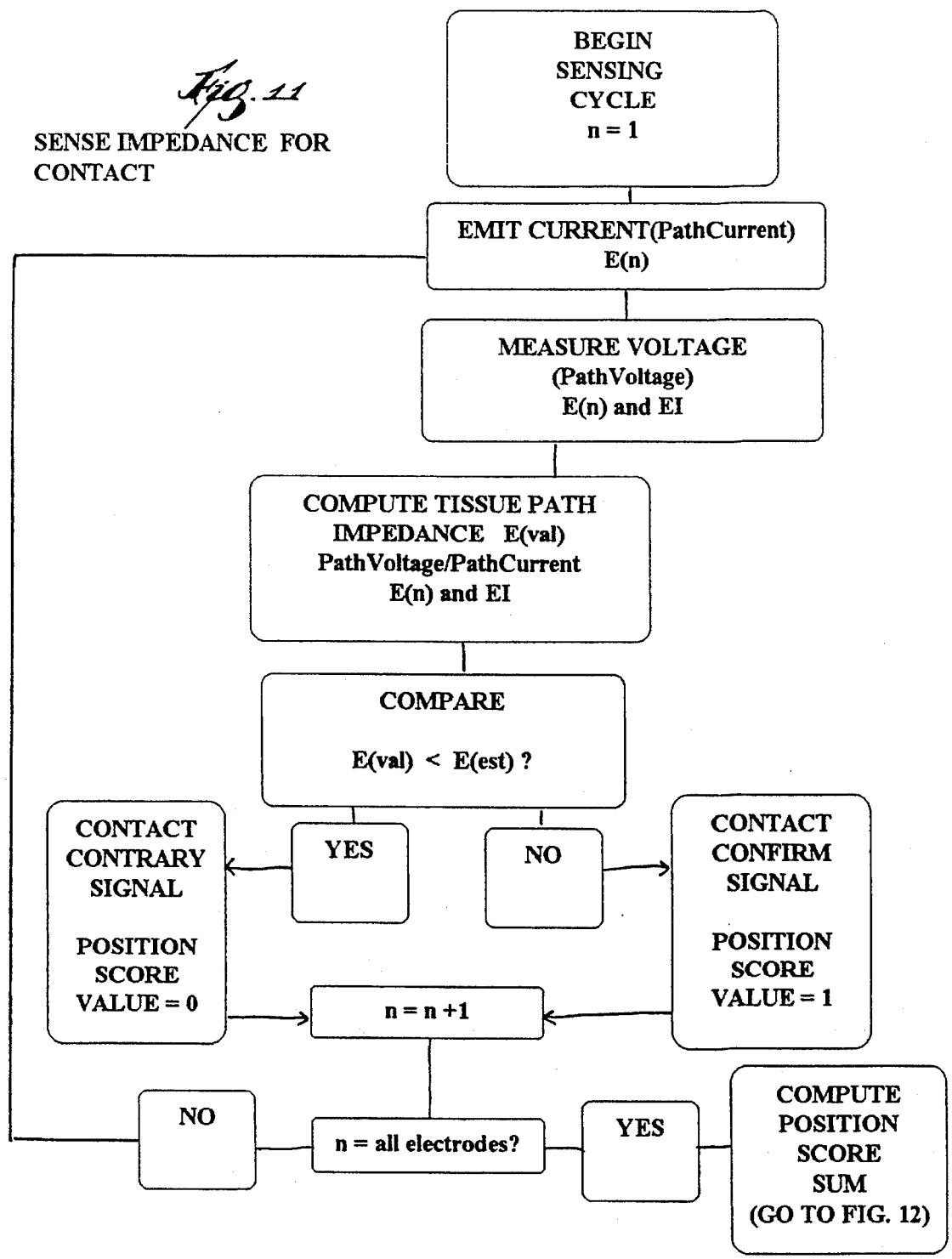
FIG. 11 is a flow chart showing the operation of the contact sensing module shown in FIG. 9, being used to sense individual electrode contact by tissue impedance measurements.

One preferred implementation of this embodiment (see FIG. 11) maintains contact between the support assembly 20 and the myocardium while deriving the impedance values.

The implementation computes tissue path impedance using the following equation:

$$\text{Impedance (ohms)} = \frac{\text{PathVoltage (volts)}}{\text{PathCurrent (amps)}}$$

The PathVoltage and PathCurrent are both root mean squared (RMS) values.

The voltage is measured in succession between each electrode and the indifferent electrode (or between EI and E(n), where n represents the location of the current emitting electrode). The impedance computed reflects not only the impedance of the underlying myocardium, but also includes the impedance of the other tissue mass in the path. The computed impedance therefore is not the actual impedance of the myocardium itself. Rather, it provides a relative scale of impedance differences of the myocardium lying in contact with the electrodes.

The CPU 42 compares the computed impedance $E_{VAL}$ for each electrode to a prescribed impedance value $E_{EST}$.

The value $E_{EST}$ should account for the resistivities of blood and viable myocardium at the frequency of the emitted current. For example, blood resistivity is about 150 ohm·cm, while viable myocardium resistivity is about 450 ohm·cm (infarcted myocardium resistivity is about 250 ohm·cm). If the indifferent electrode EI is an external 40 cm² patch electrode, $E_{EST}$ is about 150 ohms. Other values could be used for other electrode geometries. If the computed impedance value $E_{VAL}$ equals or exceeds the prescribed value $E_{EST}$, the CPU 42 infers sufficient electrical contact at that electrode site and generates a unitary contact-confirm signal. If the computed impedance value $E_{VAL}$ is less than the prescribed value $E_{EST}$, the processing system infers a lack of sufficient electrical contact at that electrode site and generates a unitary contact-contrary signal.

The unitary contact-confirm and contactcontrary signals are specific to each electrode site. The physician can use each of these site specific signals to position the support assembly to obtain the best site specific electrical contact.

Alternatively, or at the same time (see FIG. 12), the CPU 42 provides the physician with an overall assessment of electrode contact for the support assembly. In this implementation, if the computed impedance value $E_{VAL}$ equals or exceeds the prescribed value $E_{EST}$, the CPU 42 assigns a position score value of 1, indicating sufficient electrical contact at that electrode site. If the computed impedance value $E_{VAL}$ is less than the prescribed value $E_{EST}$, the CPU 42 assigns a position score value of 0, indicating the lack of sufficient electrical contact at that electrode site.

The CPU 42 computes the sum of the position score values obtained (ΣPS). The CPU 42 then compares the position score value sum ΣPS to the total number of electrodes sampled (ΣE). From this comparison, the CPU 42 creates a contact value $C_{VAL}$, which is computed as follows:

$$C_{VAL} = \frac{\Sigma PS}{\Sigma E} \times 100$$

In this implementation, as with the previously described embodiment, the CPU 42 compares the contact value $C_{VAL}$ to a predetermined value $C_{EST}$ to generate the compound contact-indicating output.

If the contact value $C_{VAL}$ equals or exceeds the predetermined value $C_{EST}$, the CPU 42 generates a compound contact-confirming signal. The compound contact-confirming signal indicates to the physician that enough electrodes 38 on the support structure 20 are in sufficient electrical contact with the myocardium to perform a reliable mapping procedure.

If the contact value $C_{VAL}$ lies below the predetermined value $C_{EST}$, the CPU 42 generates a compound contact-contrary signal. The compound contact-contrary signal indicates to the physician that the electrodes 38 on the support structure 20 are not in sufficient contact with the myocardium to perform a reliable mapping procedure. The compound contact-contrary signal-suggests that the physician should relocate the support assembly 20.

As before stated, the predetermined contact value $C_{EST}$ can vary according to the physiology of the patient, the structure of the electrode support assembly 20, and the medical judgement of the physician.

For reasons stated above, it is believed that an acceptable $C_{EST}$ lies in the range of about 50 to 100. A realistic target for $C_{EST}$ is believed to lie at or above 85 for most procedures.

In either situation, the module 36(2) allows the physician to generate another cycle to confirm the compound contact-indicating output.

(ii) Comparative Blood/Tissue Impedance

FIGS. 13 and 14 show an alternate embodiment of a multiple electrode assembly 94 whose contact with the myocardium can be electrically determined by differential tissue impedance measurements.

Like the assembly 20 shown in FIG. 1, the assembly 94 comprises an array of flexible spline elements 96 assembled to form a three dimensional structure carried on the distal end 16 of the catheter tube 12. Like the assembly 20, the spline elements 96 of the assembly 94 carry an array of electrodes 98. The electrodes 98 are mounted to each spline 22 to maximize surface contact with endocardial tissue, while at the same time minimizing exposure to the surrounding blood pool, as FIG. 10 shows.

Unlike the assembly 20, which used the outer sheath 40 to collapse the spline elements 22, the assembly 94 includes a center wire 100 to alter the shape of the structure. The distal end of the wire 100 connects to the hub 102 of the assembly 94. The wire 100 passes through the catheter tube 12 into the handle 104, where its proximal end attaches to a control lever 106.

As FIG. 13 shows, pushing the control lever 106 forward causes the wire 100 to straighten the splines elements 96 inward. This causes at least a partially collapse or elongation of the support assembly 94 within the heart chamber 30. This in turn pulls the electrodes 98 away from electrical contact with the myocardium. Instead, the electrodes 98 are mostly exposed to the blood pool in the chamber 30.

As FIG. 14 shows, pulling back on the control lever 106 causes the wire to bend the spline elements 96 outward. The support assembly 94 expands to its intended fully deployed condition, urging the electrodes 94 toward electrical contact with the myocardium.

Used in association with the support assembly 94, the contact sensing module 36(2) is conditioned by the CPU 42 to measure the relative change in impedance values when the support assembly 94 is opened to contact heart tissue (as in FIG. 14) and when the support assembly 94 is partially collapsed to contact blood (as in FIG. 13). The CPU 42 generates a contact-indicating output based upon the measured change in impedance values.

As FIG. 15 shows, the CPU 42 prompts the physician to move the control lever 106 forward to urge the electrodes 98 into the blood pool (as FIG. 13 shows). With the support assembly 98 in this condition, the CPU 42 conditions the module 36(2) to transmit an electrical current in succession through all or at least a significant number of electrodes 98, in the manner previously described. The CPU 42 computes the impedance, which represents blood path impedance BloodPathImp, since most of the electrode 98 are exposed to the blood pool. BloodPathImp is calculated as follows:

$$\text{BloodPathImp (ohms)} = \frac{\text{BloodPathVoltage (volts)}}{\text{BloodPathCurrent (amps)}}$$

The BloodPathVoltage and BloodPathCurrent are both root mean squared (RMS) values.

The voltage is measured in succession between each electrode and the indifferent electrode (or between EI and E(n), where n represents the location of the current emitting electrode).

As FIG. 16 shows, the CPU 42 then prompts the physician to move the control lever 106 rearward to urge the electrodes 98 into electrical contact with the myocardium (as FIG. 14 shows). With the support assembly 98 in this condition, the CPU 42 conditions the module 36(2) to again transmit an electrical current in succession through the same electrodes that emitted current when the support assembly 94 was collapsed in the blood pool. The CPU 42 computes impedance, which this time represents tissue path impedance TissuePathImp.

The CPU 42 computes TissuePathImp using the following equation:

$$\text{TissuePathImp (ohms)} = \frac{\text{TissuePathVoltage (volts)}}{\text{TissuePathCurrent (amps)}}$$

As before, the TissuePathVoltage and TissuePathCurrent are both root mean squared (RMS) values.

As before, the voltage is measured in succession between each electrode and the indifferent electrode (or between EI and E(n), where n represents the location of the current emitting electrode).

Figure 17:
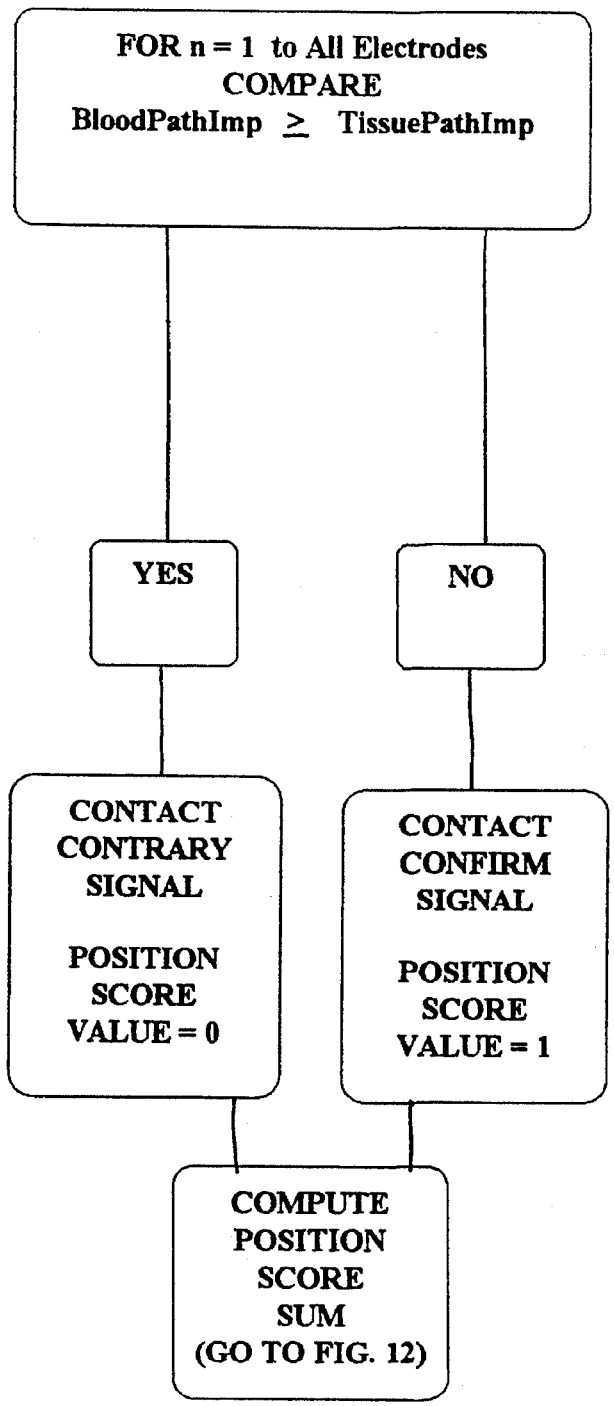
FIG. 17 is a flow chart showing the operation of a contact sensing module usable in association with the multiple electrode structure shown in FIGS. 13 and 14 comparing sensed tissue path impedance and sensed blood path impedance to derive contact-indicating signals.

As FIG. 17 shows, the CPU 42 compares the derived TissuePathImpedance for each electrode with the derived BloodPathImpedance for that electrode. The processing system derives the change in the impedance ($\Delta$IMP), as follows:

$$\Delta IMP = \frac{\text{TissuePathImp} - \text{BloodPathImp}}{\text{BloodPathImp}} \times 100$$

For each electrode 98 that emitted current, the CPU 42 compares $\Delta$IMP to a prescribed difference value $\Delta$EST. If $\Delta$IMP equals or exceeds $\Delta$EST, the CPU 42 infers sufficient electrical contact between the electrode and the myocardium. In this circumstance, the CPU 42 generates a unitary contact-confirm signal. If $\Delta$bIMP is less than $\Delta$EST, the CPU 42 infers that sufficient electrical contact does not exist. In this circumstance, the CPU 42 generates a unitary contact-contrary signal.

The unitary contact-confirm and contactcontrary signals in this implementation are also specific to each electrode. The physician can use each of these site specific signals to position the support assembly to obtain the best site specific electrical contact.

Alternatively, or at the same time, the CPU 42 can provide the physician with an overall assessment of electrode contact for the support assembly 98. In this implementation (see FIG. 17), if $\Delta$IMP equal or exceeds $\Delta$EST, the CPU 42 assigns a position score value of 1, indicating sufficient electrical contact at that electrode site. If $\Delta$IMP is less than $\Delta$EST, the CPU 42 assigns a position score value of 0, indicating the lack of sufficient electrical contact at that electrode site.

Figure 12:
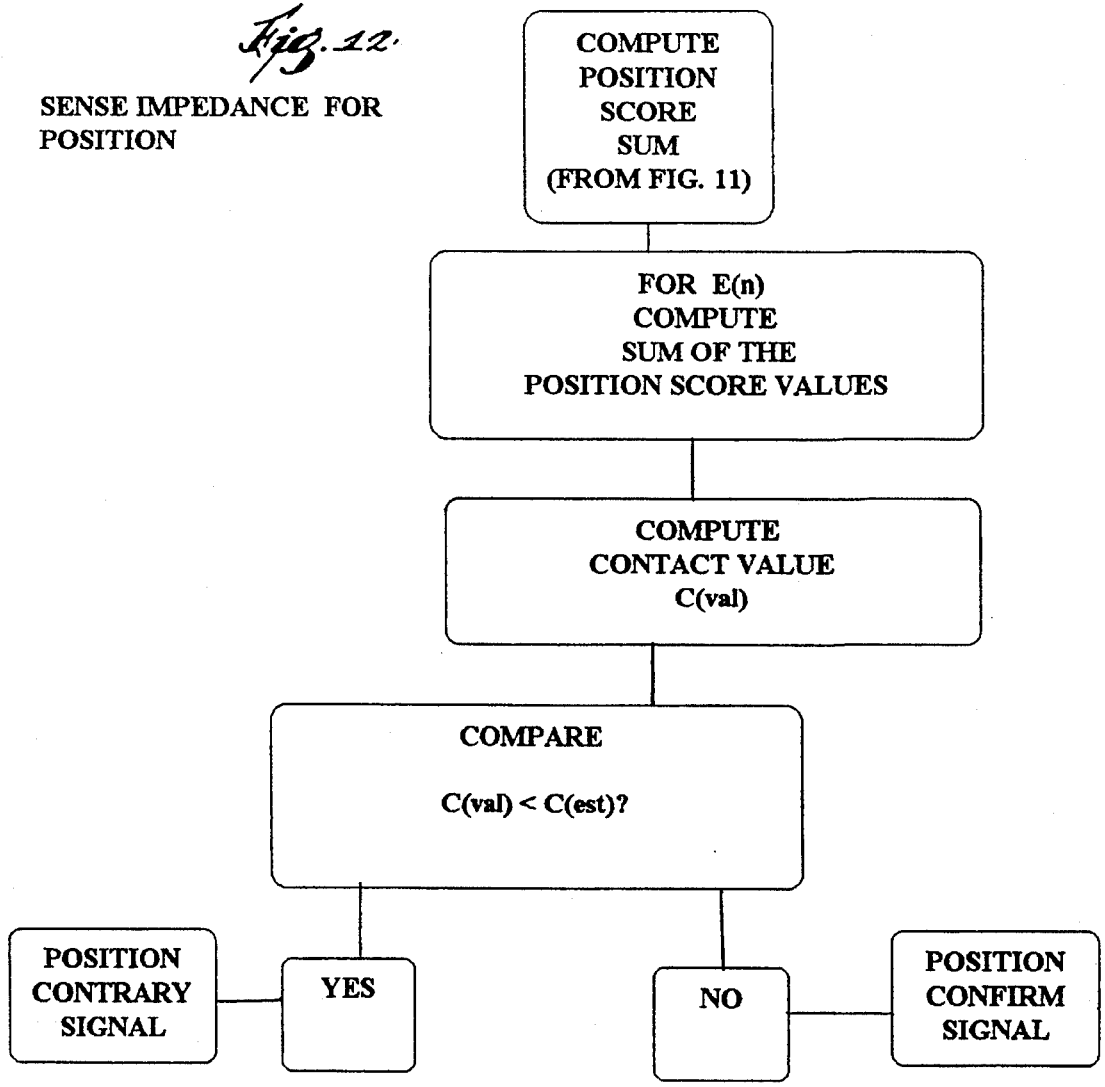
FIG. 12 is a flow chart showing further operation of the contact sensing module shown in FIG. 9, being used to assess composite contact of the multiple electrode structure by tissue impedance measurements.

The CPU 42 then computes the sum of the position score values obtained ($\Sigma$PS), as before described and as shown in FIG. 12. Also as before described and shown in FIG. 12, the CPU 42 then compares the position score value sum $\Sigma$PS to the total number of electrodes sampled ($\Sigma$E). From this comparison, the signal processing system creates a contact value $C_{VAL}$, which is compared to the predetermined contact value $C_{EST}$ to generate either a position contrary signal or a position confirm signal, as previously described. As before stated, a realistic value for $C_{EST}$ for most procedures is believed to lie at or above 85.

The features of the invention are set forth in the following claims.

We claim:

1. A system for evaluating electrical contact between the myocardium and a multiple electrode array inside the heart, the multiple electrode array comprising first and second circumferentially spaced splines for contacting circumferentially spaced endocardial regions, each spline supporting at least one electrode, the system comprising first means for electrically sensing electrical contact between at least one electrode on the first spline and the myocardium and for generating a first unitary contact-indicating output indicating the presence or absence of the electrical contact, and second means, operable independently of the first means, for electrically sensing electrical contact between at least one electrode on the second spline and the myocardium and for generating a second unitary contact-indicating output indicating the presence or absence of the electrical contact, at least one of the first and second means being operable to sense electrical contact by emitting from the respective electrode an electrical signal that activates the myocardium.

2. A system according to claim 1 and further including third means for correlating the first and second unitary contact-indicating outputs to generate a compound contact-indicating output indicating the aggregate electrical contact between the myocardium and the multiple electrode array.

3. A system according to claim 1 wherein the one first or second means emits a pacing signal from the respective electrode and senses electrical contact by sensing electrograms.

4. A system according to claim 1 and further including means for conditioning at least one electrode on the first and second splines to emit a therapeutic signal into the myocardium.

5. A system according to claim 1 and further including means for conditioning at least one electrode on the first and second splines to obtain a diagnostic signal from the myocardium.

6. A system for evaluating electrical contact between the myocardium and a multiple electrode array within the heart, the multiple electrode array comprising first and second circumferentially spaced splines for contacting circumferentially spaced endocardial regions, each spline supporting at least one electrode, the system comprising an energy generating element for electrical connection to at least one electrode on each support spline to emit electrical energy into the myocardium through the electrodes, and a signal acquisition element adapted to be electrically coupled to the emitting electrodes for detecting, independently for each emitting electrode, at least one acquired signal resulting from the emission of electrical energy by the respective electrode, the acquired signal varying with electrical contact between the respective emitting electrode and the myocardium to differentiate between the presence of the electrical contact and the absence of the electrical contact.

7. A system according to claim 6 and further including means for comparing the acquired signal for each emitting electrode with an expected signal to determine the presence or absence of the electrical contact.

8. A system according to claim 6 and further including a processing element electrically coupled to the signal acquisition element that, independently for each emitting electrode, compares the acquired signal for each emitting electrode with an expected signal.

9. A system according to claim 8 and further including an output element for generating, independently for each emitting electrode, a unitary contact-indicating output for the respective emitting electrode based upon the comparison, the unitary contact-indicating output indicating the presence or absence of the electrical contact.

10. A system according to claim 9 wherein the output element generates, independently for each emitting electrode, a unitary contact-confirm output for the respective electrode if the acquired signal for the respective electrode compares with the expected signal and a unitary contact-contrary output for the respective electrode if the acquired signal does not compare with the expected signal.

11. A system according to claim 9 wherein the processing element correlates the independent unitary contact-indicating output for each emitting electrode to derive a compound contact-indicating output indicating the aggregate of the electrical contact for the multiple electrode array.

12. A system according to claim 6 wherein the energy generating element generates electrical energy that does not activate the myocardium.

13. A system according to claim 12 wherein the generated electrical energy is an electric current, and wherein the signal acquisition element detects tissue impedance.

14. A system according to claim 6 wherein the energy generating element generates electrical energy that activates the myocardium.

15. A system according to claim 14 wherein the generated electrical energy is a pacing signal, and wherein the signal acquisition element detects electrograms.

16. A system according to claim 6 and further including means for conditioning at least one electrode on the first and second support splines to emit a therapeutic signal into the myocardium.

17. A system according to claim 6 and further including means for conditioning at least one electrode on the first and second support splines to obtain a diagnostic signal from the myocardium.

18. A system for evaluating electrical contact between the myocardium and an electrode inside the heart comprising an energy generating element for electrical connection to the electrode to emit electrical energy into the myocardium through the electrode that activates the myocardium, a signal acquisition element adapted to be electrically coupled to the electrode for detecting at least one acquired signal resulting from the emission of electrical energy by the electrode, the acquired signal varying with electrical contact between the electrode and the myocardium to differentiate between electrical contact and the absence of electrical contact, a processing element electrically coupled to the signal acquisition element to compare the acquired signal for the electrode with an expected signal, and an output element for generating a contact-indicating output for the electrode based upon the comparison, the contact-indicating output indicating the presence or absence of electrical contact between the electrode and the myocardium.

19. A system according to claim 18 wherein the acquired signal is an electrogram.

20. A system for evaluating electrical contact between the myocardium and multiple electrodes inside the heart comprising an energy generating element for electrical connection to the electrodes to emit electrical energy into the myocardium in a predetermined sequence through at least two electrodes, a signal acquisition element adapted to be electrically coupled to the electrodes for detecting, independently for each emitting electrode, at least one acquired signal resulting from the emission of electrical energy by the respective electrode, the acquired signal varying with electrical contact between the respective electrode and the myocardium to differentiate between the presence of the electrical contact and the absence of the electrical contact, a processing element electrically coupled to the signal acquisition element that compares, independently for each emitting electrode, the acquired signals for the respective electrode with an expected signal, and an output element for generating, independently for each emitting electrode, a contact-indicating output for the respective electrode based upon the comparison.

21. A system according to claim 20
wherein the energy generating element generates electrical energy that activates the myocardium.

22. A system according to claim 21
wherein the acquired signal is an electrogram.

23. A system according to claim 20
wherein the energy generating element generates electrical energy that does not activate the myocardium.

24. A system according to claim 23
wherein the acquired signal is a tissue impedance measurement.

25. A method for evaluating electrical contact between the myocardium and a multiple electrode array inside the heart comprising the steps of deploying a multiple electrode array into a chamber of the heart, the array comprising first and second circumferentially spaced splines for contacting circumferentially spaced endocardial regions, each spline supporting at least one electrode, electrically sensing electrical contact between at least one electrode on the first spline and the myocardium in a first endocardial region to generate a first unitary contact-indicating output indicating the presence or absence of the electrical contact in the first region, and electrically sensing electrical contact between at least one electrode on the second spline and the myocardium in a second endocardial region circumferentially spaced from the first region to generate a second unitary contact-indicating output indicating the presence or absence of the electrical contact in the second region, wherein, in electrically sensing electrical contact, the respective electrode is caused to emit an electrical signal that activates the myocardium.

26. A method according to claim 25
and further including the step of correlating the first and second unitary contact-indicating outputs to generate a compound contact-indicating output indicating the aggregate of the electrical contact between the myocardium and the multiple electrode array.

27. A method according to claim 25
wherein, in electrically sensing electrical contact, electrograms are sensed.

28. A method according to claim 25
wherein the steps of electrically sensing electrical contact comprises the steps of
emitting electrical energy into the myocardium independently through the electrodes, and
detecting, independently for each emitting electrode, at least one acquired signal resulting from the emission of electrical energy by the respective electrode, the acquired signal varying with electrical contact between the respective emitting electrode and the myocardium to differentiate between the presence of the electrical contact and the absence of the electrical contact.

29. A method according to claim 28
wherein the steps of generating the first and second unitary contact-indicating outputs include comparing the acquired signal for each emitting electrode with an expected signal to determine the presence or absence of the electrical contact.

30. A method according to claim 29
wherein the steps of generating the first and second unitary contact-indicating outputs include generating, independently for each emitting electrode, a unitary contact-confirm output for the respective electrode if the acquired signal for the respective electrode compares with the expected signal and a unitary contact-contrary output for the respective electrode if the acquired signal does not compare with the expected signal.

31. A method according to claim 25
and further including the step of conditioning at least one electrode on the first and second support splines to emit a therapeutic signal into the myocardium.

32. A method according to claim 25
and further including the step of conditioning at least one electrode on the first and second support splines to obtain a diagnostic signal from the myocardium.

* * * * *